US007786306B2

(12) United States Patent
Chen et al.

(10) Patent No.: US 7,786,306 B2
(45) Date of Patent: Aug. 31, 2010

(54) PROCESS FOR RESOLVING CHIRAL PIPERIDINE ALCOHOL AND PROCESS FOR SYNTHESIS OF PYRAZOLO[1,5-A] PYRIMIDINE DERIVATIVES USING SAME

(75) Inventors: Frank Xing Chen, Plainsboro, NJ (US); Maria M. Tamarez, Rahway, NJ (US); Ji Xie, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 270 days.

(21) Appl. No.: 11/893,850

(22) Filed: Aug. 17, 2007

(65) Prior Publication Data

US 2008/0051579 A1 Feb. 28, 2008

Related U.S. Application Data

(60) Provisional application No. 60/838,691, filed on Aug. 18, 2006.

(51) Int. Cl.
*C07D 487/00* (2006.01)
*C07D 211/00* (2006.01)
(52) U.S. Cl. .................................. 546/184; 544/281
(58) Field of Classification Search ................ None
See application file for complete search history.

(56) References Cited

U.S. PATENT DOCUMENTS 7,119,200 B2   10/2006   Guzi et al.
2004/0209878 A1   10/2004   Guzi et al.
2004/0210060 A1   10/2004   Delplanche et al.

OTHER PUBLICATIONS

Price et al. Journal of the American Chemical Society, 82, 2613-2616, 1960.*
International Search Report, PCT/US2007/018289; mailed Jan. 23, 2008; 3 pages.
Toy; Price; "d- and l-Polyconidine", Journal of the American Chemical Society; vol. 82, 1960; pp. 2613-2616; XP-002464237.
Danilewicz, J.C.;et. al.; "Design of Selective Thrombin Inhibitors Based on the (R)-Phe-Pro-Arg Sequence"; *J. Med. Chem.*; 2002; 45(12) pp. 2432-2453.
Ekborg-Ott, K.H.; et. al.; "Highly Enantioselective HPLC Separations Using the Covalently Bonded Macrocyclic Antibiotic, Ristocetin A, Chiral Stationary Phase", *Chirality*; 1998; 10; pp. 434-483.
Menche, D.;et. al.; "Design, synthesis and biological evaluation of novel analogues of archazolid: A highly potent simplified V-ATPase inhibitor"; *Bioorganic and Medicinal Chemistry Letters*; 2007; 17; pp. 1732-1735.
Morley, C., et, al.; "Complementary Enantioselective Approaches to the Quinolizidine Alkaloids Lupinine and Epilupinine by Elonate Claisen Rearrangements or Direct Allylation of Piperidin-2-ylacetuc Acid Derivatives", *J. Chem. Soc., Perkin Transactions I*; 1994; 63, p. 2903-2907.
Toy, M.S.;et. al.; "d- and l-Polyconidine"; *J. Am. Chem. Soc.*;1960; 82 ; pp. 2613-2616.

* cited by examiner

*Primary Examiner*—D. Margaret Seaman
*Assistant Examiner*—Nizal S Chandrakumar
(74) *Attorney, Agent, or Firm*—Gerard Devlin; H. Eric Fischer

(57) ABSTRACT

The present invention provides a method of resolving piperdin-yl-alkylene-alcohols, in high yield at high enantiomeric purity, for example 2-piperidin-2-yl-ethanol.

39 Claims, No Drawings

PROCESS FOR RESOLVING CHIRAL PIPERIDINE ALCOHOL AND PROCESS FOR SYNTHESIS OF PYRAZOLO[1,5-A] PYRIMIDINE DERIVATIVES USING SAME

CROSS-REFERENCE TO RELATED APPLICATIONS

The present application is based on and claims the priority of U.S. Provisional Application No. 60/838,691 filed Aug. 18, 2006, which is incorporated herein by reference in its entirety.

FIELD OF THE INVENTION

This application discloses a novel process to resolve mixtures of enantiomers of 2-Piperidin-2-yl-ethanol and its use in the preparation of 3-alkyl-5-piperidin-1-yl-3,3a-dihydro-pyrazolo[1,5-a]pyrimidin-7-yl)-amino derivatives, which have utility, for example, as pharmaceutically active compounds having CDK2 inhibitor activity.

BACKGROUND OF THE INVENTION

Identification of any publication in this section or any section of this application is not an admission that such publication is prior art to the present invention.

The preparation of compounds of Formula I, for example, the compounds of Formula III, has been described in Published U.S. Patent Application No. 2004-0209878 A1, filed on Feb. 11, 2004 (the '878 publication), which is incorporated herein by reference.

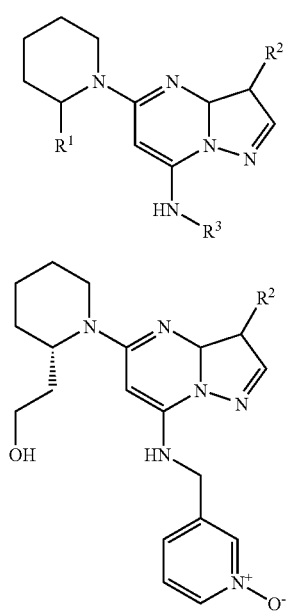

Formula I

Formula III wherein $R^1$ is a linear, branched, or cyclic alkyloxy functional group of the structure (—$R^{2a}$—OH), $R^{2a}$ is a linear, branched or cyclic alkylene group, $R^2$ is a linear, branched or cyclic alkyl group, and $R^3$ is an alkylene-heterocycle, for example, the 3-methylene-pyridine-N-oxide substituent shown in the structure of Formula III. These compounds are believed to have pharmaceutical activity as compounds having cyclin-dependent kinase inhibitor (CDK inhibitor) properties.

As described in the '878 publication, the compounds of Formula I can be prepared through the general routes described below in Scheme I.

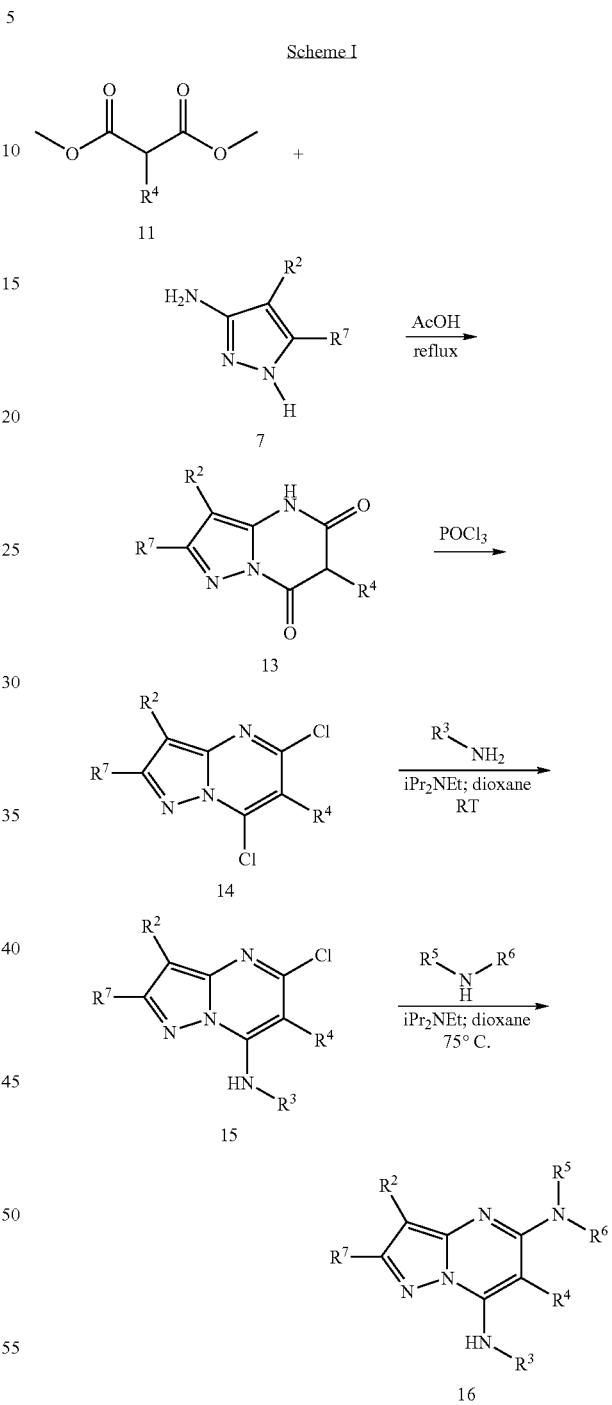

Scheme I

Where $R^1$, $R^2$, and $R^3$ are as defined above, $R^4$ and $R^7$ are H, or $R^2$ and $R^5$ and $R^6$ are taken together to form an alkyl heterocycle, for example, pyrimidin-1-yl, optionally substituted on any carbon with a linear, branched, or cyclic alkyl, which is optionally substituted with hydroxide.

One of these inhibitor compounds of particular interest for its CDK inhibiting activity is the compound of Formula II.

Formula II

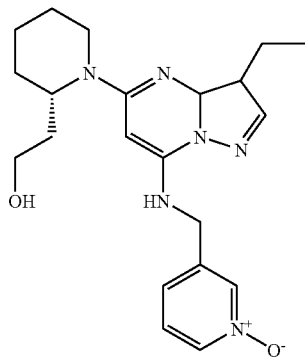

As described in detail in the '878 publication, in Example 500, on pages 334 to 343, the compound of Formula II can be synthesized in accordance with Scheme II:

Scheme II:

Step 1 - substituted pyrazole formation.

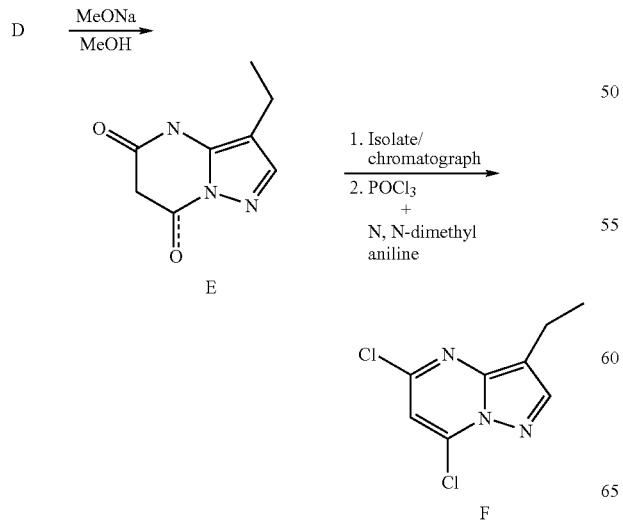

Step 2 - dihalogenated pyrazolo[1,5-a]pyrimidine formation.

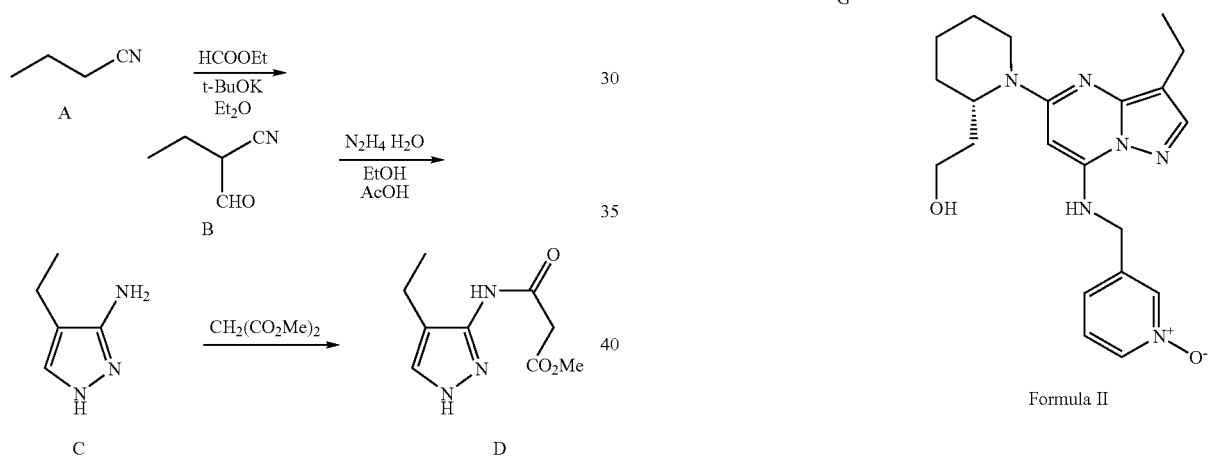

Step 3 - amination (two separate, sequential reactions)

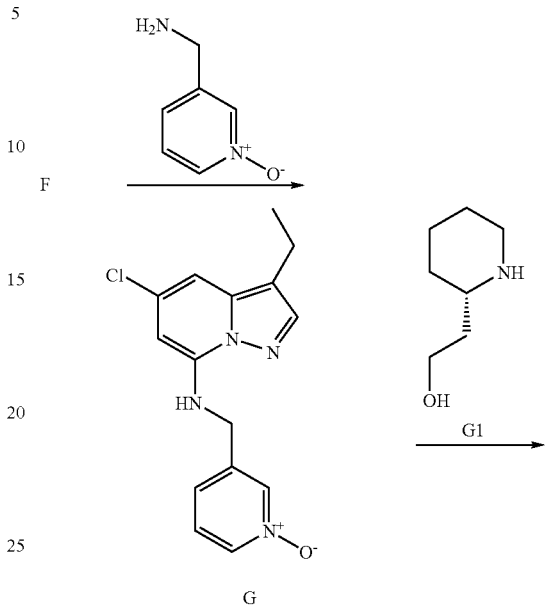

Formula II

In the second amination reaction of Step 3 of the Scheme II synthesis, the chiral alcohol reagent (S)2-piperidin-2-yl ethanol (compound G1) is reacted with (5-Chloro-3-ethyl-pyrazolo[1,5-a]pyridin-7-yl)-(1-oxy-pyridin-3-ylmethyl)-amine (compound G) to yield the compound of Formula II.

The chiral alcohol (G1) is commercially available as a mixture of R and S isomers. Resolution of these isomers has been accomplished by complexing the alcohol with d-10-champhorsulfonic acid (the compound of the structure of Formula G2a) and crystallizing the complexed alcohol from ethanol in accordance with a literature procedure published in the Journal of the American Chemical Society, 82, pp 2613 to 2616 (1960).

Formula G2a

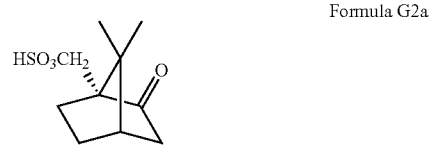

Resolution of 2-piperidin-2-yl ethanol by this method has also been reported in the Journal of Medicinal Chemistry, 45, p 2432, Bioorganic and Medicinal Chemistry Letters, 10, 1732 (2000), Chirality, 10, p 434 (1998), and the Journal of the Chemistry Society, Perkin Transactions I, 63, p 2903 (1994). This published procedure generally provides the alcohol in a yield of less than 17% based on the mixed isomer starting alcohol, and typically produces the desired isomer in yields of less than 10% based on the starting alcohol. When using this procedure, generally numerous sequential recrystallizations are required to achieve enantiomeric purity of 95% enantiomeric excess (ee) or more, which diminishes the yield of the desired isomer. Enantiomeric purity is calculated by subtracting the weight of the minority isomer from the weight of the predominant isomer present in a sample, and dividing the difference by the sum of the minority and predominant isomers present in the sample. Accordingly, a sample having 97.5 wt. % of the S isomer and 2.5 wt. % of the R isomer has an enantiomeric purity of 95% ee. In the synthesis of CDK inhibitor compounds described above, it is desirable to utilize the desired isomer of piperidine-ethanol starting materials having more than about 97% ee purity.

OBJECTIVES AND SUMMARY OF THE INVENTION

In view of the foregoing, what is needed is a resolution process for preparing the critical intermediate 2-piperidin-2-yl ethanol useful in the synthesis of CDK inhibitor compounds that provides the alcohol in high enantiomeric purity, high chemical purity, and in yields of more than about 17%. These and other objectives and/or advantages are provided by the present invention.

In one aspect the present invention is a process for providing 2-piperidin-2-yl ethanol in an enantiomeric excess (ee) of at least about 95% utilizing a single crystallization step, the process comprising:

(a) combining a solution comprising a polar, aprotic organic solvent and a mixture of isomers of 2-piperidin-2-yl-ethanol with an aliphatic alcohol solution containing an amino acid resolving agent selected from N-acetyl-L-leucine and N-acetyl-L-methionine;

(b) mixing the combined solutions with additional amounts of the polar, aprotic organic solvent and warming the mixture to a temperature below the boiling point of either solvent in the mixture sufficient to promote dissolution of any solids present in the mixture;

(c) cooling the mixture to a temperature which permits salt precipitation therefrom;

(d) optionally isolating the precipitated salt formed in step "c"; and (e) optionally purifying the isolated salt from Step "d" by recrystallization or slurrying with a purifying solvent.

In some embodiments it is preferred for the polar, aprotic organic solvent in Step "a" to be selected from tetrahydrofuran (THF), acetonitrile (ACN), acetone, and ethylacetate, more preferably the polar, aprotic organic solvent is THF. In some embodiments it is preferred to select the aliphatic alcohol in Step "a" from alcohols having 5 carbon atoms or less, more preferably, the aliphatic alcohol is methanol. In some embodiments it is preferred to use a volumetric ratio of polar aprotic organic solvent (PAO solvent):aliphatic alcohol of from about 20:1 PAO solvent:aliphatic alcohol to about 2:1 PAO solvent:aliphatic alcohol, more preferably from about 19:1 PAO solvent:aliphatic alcohol to about 5:1 PAO solvent: aliphatic alcohol. In some embodiments it is preferred to use a ratio of about 19:1 PAO solvent:aliphatic alcohol. In some embodiments it is preferred to use a ratio of about 5:1 PAO solvent:aliphatic alcohol.

In some embodiments of the present invention, purification step "e" is a recrystallization carried out in a mixed solvent, preferably a mixture of acetonitrile (ACN) and methanol (MeOH) selected with a ratio of the component suitable for dissolving the salt at a temperature above ambient and precipitating the salt when the temperature is reduced, preferably to a point below ambient. In some embodiments the purification step "e" is conducted by slurrying the precipitate provided in step "d" with a solvent in which the unwanted constituents are soluble but the desired salt is not soluble to any great extent, thereby leaving the desired salt undissolved thereby separating the desired salt and the impurities coprecipitated in step "d". When purification Step "e" constitutes slurrying, preferably a solvent mixture is used having a volumetric ratio of from about 10:1, ACN:MeOH to a volumetric ration of about 20:1 ACN:MeOH. In some embodiments purification step "e" is repeated until the desired ee value is obtained.

In some embodiments of the invention which include a precipitation step "d" the process further includes isolation of the precipitated salt from step "d", redissolving, or partially redissolving the salt in a solvent and liberating the alcohol free base prior to using the alcohol in a reaction by treatment of the solution or slurry with a base. In some embodiments which include a purifying step "e" the process further includes isolating the purified salt from step "e", redissolving or partially dissolving the salt and liberating the alcohol free base prior to using the alcohol in a reaction. In some embodiments of the invention including a precipitation step "d" or a precipitation step "d" followed by a purification step "e", the process further includes utilizing the salt produced in step "d" or in step "e" directly in a reaction and liberating the alcohol free base therefrom in situ in the reaction mixture.

In some embodiments of the present invention it is preferred to use N-acetyl-L-leucine as the resolving agent. In some embodiments of the invention, it is preferred to use a methanol solution having a resolving agent concentration which is at least 1 M in resolving agent, more preferably from about 3 M to about 10 M in resolving agent, and more preferably about 5 M in resolving agent. In some embodiments of the invention it is preferred to provide a THF solution in step "a" of the resolving process having a concentration of 2-piperidin-2-yl-ethanol which is at least about 0.05 M, more preferably from about 1 M to about 5 M, and more preferably has about a 2 M concentration in 2-piperidin-2-yl-ethanol.

In some embodiments it is preferred to maintain the methanol solution and the combined methanol and THF solutions in step "a" at a temperature of from about 35° C. to about 40° C. In some embodiments it is preferred in step "b" of the resolution process to warm the combined and diluted solutions to a temperature of from about 50° C. to about 55° C. In some embodiments of the invention it is preferred to cool the solution in step "c" to a temperature of at least 15° C., more preferably to cool the solution to a temperature of from about 10° C. to about 15° C.

In some embodiments utilizing purification step "e" it is preferred to slurry the precipitate from step "d" by heating a mixture of the precipitated salt from step "d" with a mixed solvent comprising about 1 vol. eq. of methanol and about 20 vol. eq. of acetonitrile to a temperature sufficient to partially dissolve the salt, preferably a temperature of about 55° C., and cooling it to a temperature of about 15° C. to precipitate purified salt.

In one aspect the present invention is part of a process for the provision of pyrazolo[1,5-a]pyrimidin-7-yl-amino compounds of Formula III having CDK inhibitor properties:

Formula III

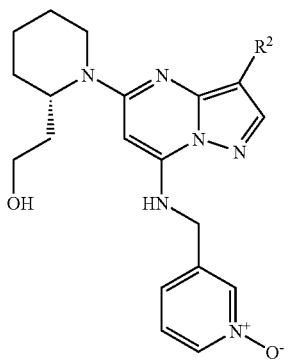

wherein $R^2$ is a linear, branched or cyclic alkyl group, the process comprising:

(a) combining a solution comprising a polar, aprotic organic solvent and a mixture of isomers of 2-piperidin-2-yl-ethanol with an aliphatic alcohol solution containing an amino acid resolving agent selected from N-acetyl-L-leucine and N-acetyl-L-methionine;

(b) mixing the combined solutions with additional amounts of the polar, aprotic organic solvent and warming the mixture to a temperature below the boiling point of either solvent in the mixture sufficient to promote dissolution of any solids present in the mixture;

(c) cooling the mixture to a temperature which permits the salt of compound G1a to precipitate therefrom, G1a

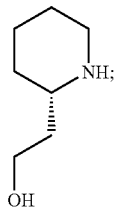

(d) purifying the salt from step "c" by a technique selected from slurrying the salt and recrystallizing the salt;

(e) liberating the free base alcohol G1a from the salt prepared in purifying Step "d"; and (f) reacting the liberated free base alcohol from Step "e" with the compound of Formula G,

G

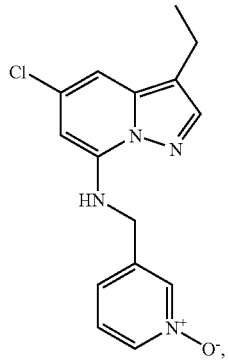

to yield a compound of Formula III.

In some embodiments it is preferred for the polar, aprotic organic solvent in Step "a" to be selected from tetrahydrofuran (THF), acetonitrile (ACN), and acetone, more preferably the polar, aprotic organic solvent is THF. In some embodiments it is preferred to select the aliphatic alcohol in Step "a" from aliphatic alcohols having 5 carbon atoms or less, more preferably, the aliphatic alcohol is methanol.

In some embodiments of the present invention, purification step "d" is carried out in a mixed solvent, preferably a mixture comprising a polar aprotic solvent selected from THF, ACN, and acetone and an aliphatic alcohol, more preferably a mixture comprising acetonitrile (ACN) and methanol (MeOH). In some embodiments it is preferred to use a mixture having a 10:1 volumetric ratio of ACN:MeOH. In some embodiments the purification step "d" is repeated until the desired ee value is obtained.

In some embodiments liberating step "e" is carried out by treating the salt in a separate solution with a base, preferably a base selected from potassium hydroxide and sodium hydroxide, thereby precipitating the free base which is isolated and added to a reaction medium in reaction step "f". In some embodiments, the liberating step "e" is carried out in situ within a reaction medium and contemporaneously reacted with a compound of Formula G.

These and other aspects of the invention will become apparent from the following detailed description.

DETAILED DESCRIPTION OF THE INVENTION

As mentioned above, and described in the '878 publication, compounds of Formula I (as defined herein) are believed to have promising activity as useful pharmaceutical compounds having CDK inhibitor properties. A synthesis of these compounds, for example, the compound of Formula II, is described in detail in published U.S. Patent Application No. 2004-0209878 A1, filed on Feb. 11, 2004 (the '878 publication). A process for providing the compound of Formula II is described in the '878 publication in Examples 507 to 508, 509, 1000 and 1001. These examples, as well as the entirety of the '878 publication are incorporated herein by reference. It will be appreciated that the present invention method for resolving chiral amino alcohol can be used in conjunction with any synthetic process requiring the use of a selected isomer of the alcohol. As mentioned above, and in the cited documents, (S)2-piperidin-2-yl-ethanol (the compound of Formula G1) is a critical intermediate in the in synthetic pathway for the preparation of compounds of Formula I, Formula II, and Formula III described in each of the aforementioned documents. The inventors have surprisingly discovered a resolving method for providing a high yield of the desired isomer in enantiomeric purity exceeding about 95% ee in a resolution process utilizing a single crystallization step. Moreover, if additional recrystallization steps are added the inventive process yields higher % ee material with recrystallized product that exceed 95% based on the starting amount of resolved alcohol recrystallized.

As used herein to describe the present invention the following terms have the following meanings.

Alkyl- is a linear, branched, or cyclic hydrocarbon substituent having a single point of attachment between the group and the substrate upon which it is a substituent. When the term Alkylene, for example methylene (—CH$_2$—), ethylene (—CH$_2$CH$_2$—), etc. is used, it is a linear branched or cyclic hydrocarbon substituent having two points of attachment, for example, as a bridge between functional groups.

The method of the present invention comprises providing separately a solution comprising the alcohol to be resolved (an amino alcohol) dissolved in a polar, aprotic organic solvent (PAO solvent) and a solution comprising the resolving agent dissolved in an aliphatic alcohol which are combined, heated and mixed with an additional amount of PAO or an amount of a solvent selected from tetrahydrofuran and acetonitrile or mixtures thereof, and then cooled to precipitate a complex of the resolving agent and the desired isomer of the amino alcohol which is being resolved. Subsequently, the precipitated complex, optionally purified by recrystallization or slurrying, is treated to liberate the free base form of the desired isomer of the resolved amino alcohol which is employed in further reactions, most usefully in the preparation of CDK inhibitor compounds. Optionally, the resolved amino alcohol complex prepared by the inventive method is used, either in "as-precipitated" form or in purified form, by introducing it directly into the reaction mixture of a subsequent reaction and liberating its free base in situ in the reaction medium.

The complex formation/precipitation step is followed by isolating the resolving agent/alcohol complex and optionally purifying the isolated complex by recrystallization or using a slurry technique. When employed, recrystallization to purify the isolated complex is carried out using a mixed solvent system of different polarity than the solvent system in which the alcohol/resolving agent complex was formed. Surprisingly, by using this methodology, higher enantiomeric purity (ee) resolved product is produced with the same number of recrystallizations when compared to prior art methods. This has the benefit of providing a high enantiomeric purity product in higher yield base on the starting alcohol to be resolved than is available with other methods. Each aspect of the methodology will be discussed next.

Resolving Agent

The present resolution method utilizes as a resolving agent either N-acetyl-L-leucine (the compound of the structure of Formula G2b)

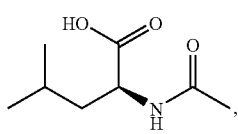

Formula G2b or N-acetyl-methionine (the compound of the structure of Formula G3b,

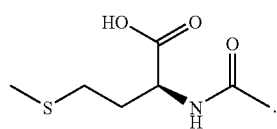

Formula G3b to form a complex with the amino alcohol to be resolved. Without being bound by theory, it is believed that the complex formed using these two resolving agents results in a greater change in polarity when it complexes with the desired amino alcohol isomer than it does when it complexes with the undesired amino alcohol isomer and/or has a higher selection for complexing with the desired amino alcohol isomer than with the undesired amino alcohol isomer, thus permitting the alcohol/resolving agent complex to be precipitated from a mixed solvent having lower polarity than the neat aliphatic alcohol comprising the mixed solvent while permitting a higher proportion of the complex of the desired isomer to be precipitated therefrom relative to the undesired isomer.

The Amino Alcohol to be Resolved

While it is believed that the method of the present invention will be most beneficial when applied to isolating in high yield and high enantiomeric purity (S)2-piperidin-2-yl-ethanol from a mixture of the "R" and "S" 2-piperidin-2-yl-ethanol isomers, other related piperidine alcohols may also be resolved using the method, for example those having the structure of Figure G4c, wherein the 2-ethanol substituent can be attached to the piperidine ring at any of the 2, 3, or 4-carbon atom position, and those having the structure of Figure G5c,

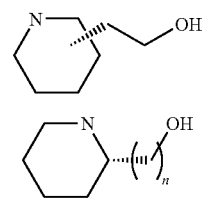

Figure G4c

Figure G5c where "n" is an integer of 1 to 4. The method is also believed to be useful for resolving 2-piperidin-2-yl-ethanol compounds of either the structure of Figure G4c or of Figure G5c having substituents on other carbon atoms of the piperidine ring in addition to the (S)2-ethanol substituent shown, for example, liner, branched or cyclic alkyl groups having less than 4 carbon atoms.

Complex Formation/Precipitation Step

The mixed solvent in which the piperidine alcohol/resolving agent complex is prepared in accordance with the present invention methodology comprises an aliphatic alcohol and a polar aprotic organic solvent (also termed herein for convenience "PAO" solvent) having less polarity than the aliphatic alcohol selected, in a ratio that provides a mixed solvent of less proton doner ability and lower polarity than the selected aliphatic alcohol alone. Accordingly, on a volumetric basis, suitable mixtures of polar aprotic organic solvent (PAO solvent) and aliphatic alcohol comprise from about 2:1 PAO solvent:aliphatic alcohol to about 10:1 PAO solvent:aliphatic alcohol, more preferably mixtures comprising a volumetric ratio of about 5:1 PAO solvent:aliphatic alcohol. In general, after mixture of the piperdine alcohol and resolving agent, the PAO solvent will act as an antisolvent and the aliphatic alcohol will act as a solvent of the salt product. Accordingly, the ratio of the PAO solvent and aliphatic alcohol are selected to strike a balance of the amount of salt product retained in solution and the amount of unwanted isomer coprecipitated with the salt product of the desired isomer. Accordingly, ratio's of aliphatic alcohol and PAO solvent lying outside of these ranges may also be used.

Examples of suitable polar, aprotic organic solvents which may be employed in the present invention resolution method include acetonitrile (ACN, Snyder solvent polarity index 6.2), acetone (Snyder solvent polarity index 5.4), ethyl acetate (Snyder solvent polarity index 4.3), tetrahydrofuran (THF, Snyder solvent polarity index 4.2) and mixtures of 2 or more of these. For resolution of (S)-2-piperidin-2-yl-ethanol, it is preferred to use THF as the polar, aprotic organic solvent.

Examples of aliphatic alcohols which may be employed in the present invention resolution method include R—OH in which "R" is a linear, branched, or cyclic alkyl group of 5 carbon atoms or less, preferably methanol (Snyder solvent polarity index 6.6), 1-propanol, 2-propanol (Snyder solvent polarity index 4.3), and ethanol (Snyder solvent polarity index 5.2). In general it is preferred to employ aliphatic alcohols having lower pKa values, for example, methanol (pKa about 15.5) and ethanol (pKa about 16) than less acidic alcohols, for example i-propanol (pKa about 16.5). In general it is preferred to employ alcohols having higher polarity on the Snyder polarity scale, for example methanol and ethanol, more preferably methanol is employed.

The amount of polar, aprotic organic solvent employed in the resolution process of the invention will be an amount sufficient to dissolve the amount of amino alcohol to be resolved. In some embodiments of the invention it is preferred to provide a PAO solvent solution in the complex formation/precipitation step of the resolving process having a concentration of the alcohol to be resolved which is at least about 0.05 M, more preferably from about 1 M to about 5 M, and more preferably has about a 2 M concentration of the amino alcohol to be resolved. When the alcohol to be resolved is 2-piperidin-2-yl-ethanol it is preferred to supply a solution of THF containing 2M concentration of 2-piperidin-2-yl-ethanol to the complex formation/precipitation step. Within these guidelines, the PAO solvent solution of amino alcohol to be resolved may be heated to effect dissolution within these guidelines.

Guided by the above-mentioned desired volumetric ratios of PAO:aliphatic alcohol, the amount of aliphatic alcohol used to provide a solution of resolving agent to the complex formation/precipitation step of the process of the invention will be at least sufficient to dissolve the resolving agent employed. It is preferred to use sufficient aliphatic alcohol to provide a solution which has a resolving agent concentration that is at least 1 M in resolving agent, more preferably from about 3 M to about 10 M in resolving agent, and more preferably about 5 M in resolving agent. Within these general guidelines, the aliphatic alcohol solution may be heated to effect dissolution of the resolving agent.

When the method of the present invention is used to resolve (S) 2-piperidin-2-yl-ethanol, it is preferably to heat the resolving agent and amino alcohol solutions to a temperature of at least 35° C. prior to combining the solutions and to maintain the temperature upon combining the solutions at a temperature of from about 35° C. to about 40° C.

Upon combination of the resolving agent aliphatic alcohol solution and the PAO solvent solution of amino alcohol to be resolved, turbidity in the mixed solutions may occur. After combination of the resolving agent and amino alcohol to be resolved, additional solvent is added to solubilize the solids produced when combining the solutions, and the mixture is heated. In general, the added solvent is selected from the PAO solvent used to dissolve the amino alcohol, however, other PAO solvents can be employed also. Preferably the PAO solvent is selected from thTHF and ACN, more preferably the less polar THF is selected.

After adding additional solvent, the mixture is heated, preferably to a temperature of at least about 50° C., but not more than the boiling point of the solvent selected. When THF is selected as the additional solvent added in this step, preferably the temperature maintained from about 50° C. to about 55° C.

After all of the solids have dissolved the solution is held at a temperature of from about 50° C. to about 55° C. for 30 minutes. The mixture is then cooled to subambient temperature to precipitate the complex, generally gradually, to control the size of the crystals precipitated from the mixture and minimize included solvent in the precipitate. When the method is utilized to prepare (S) 2-piperidin-2-yl-ethanol the cooling step is carried out over a period of about 2 hours, reducing the temperature of the mixture from a temperature of about 50° C. to about 55° C. to a temperature of about 15° C.

In another aspect, the present invention process forms a part of an improved synthesis for the preparation of pyrazolo-[1,5-a]-pyrimidine compounds carried out in accordance with Scheme III.

Scheme III

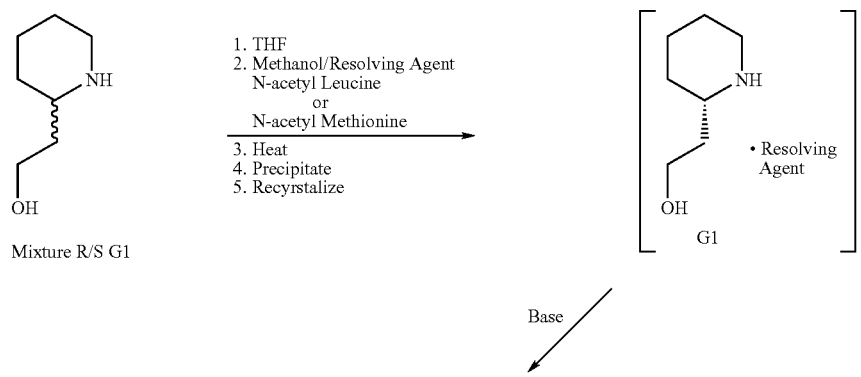

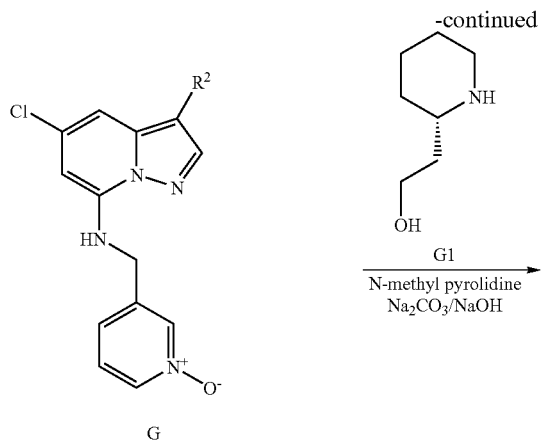

G

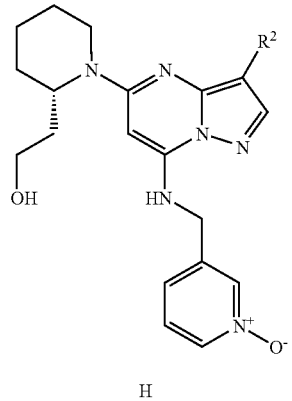

H wherein R² is a linear, branched or cyclic alkyl group, and X is selected from a halogen and a sulfonyl leaving group. Preferably R² has 4 carbon atoms or fewer, more preferably R² is an ethyl-group (—CH₂CH₃). Preferably X is chloride It will be appreciated that the present invention resolution process can be used to supply the resolved 2-piperidin-2-yl-ethanol intermediate and reacted with compounds of Formula G prepared by any known method of supplying compounds of Formula G. Particularly preferred are reaction schemes described in the above-referenced '878 publication. In some embodiments of the invention, preferably the resolution scheme of the present invention is combined with reaction schemes producing the compound of Formula III.

It will be appreciated that the above-described Scheme III can be used to prepare compounds of Formula I, Formula II, and Formula III, depending upon the structure of the (5-Chloro-3-alkyl-pyrazolo[1,5-a]pyridin-7-yl)-(1-oxy-pyridin-3-ylmethyl)-amine employed. Particularly preferred are reactions in which the R² group of the compound of Formula G is an ethyl-group and X is chloride, thereby providing the compound of Formula G1a, which yields a product of the structure of Formula II described above.

Formula G1a reaction, which utilizes the (S) isomer of 2-piperidin-2-yl-ethanol, is performed in the presence of sodium or potassium hydroxide. Accordingly, in this step the compound of Formula G1 can be provided to the reaction mixture in the form of its recrystallized salt, or in the form of the precipitated product from the previous step, which will be converted in situ to the free base, without requiring a separate step for liberating the free base prior to employing it in a reaction.

Scheme IV

Step 1 - Diketone synthesis

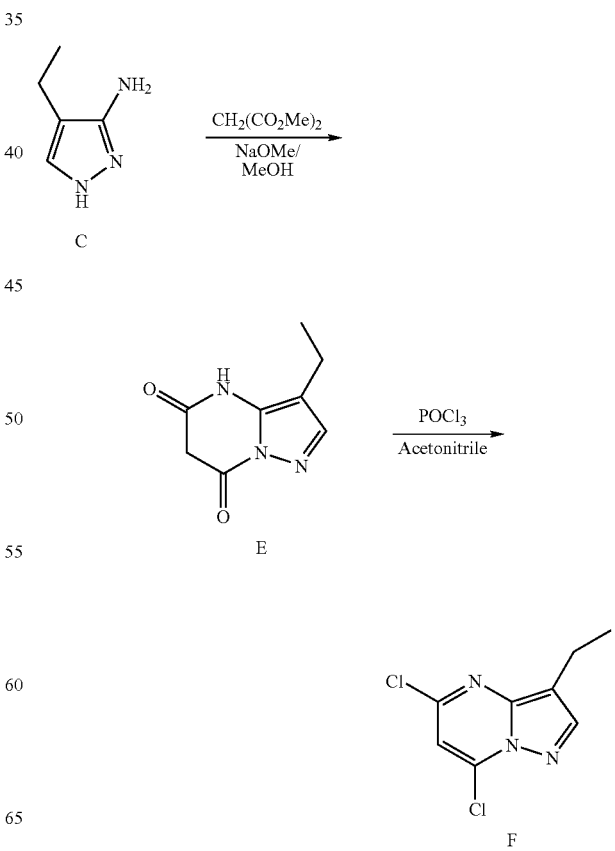

A particularly preferred scheme for preparing a compound of Formula II is shown in Scheme IV, below. It is believed that the present invention method of resolving (S) 2-piperidin-2-yl-ethanol will be especially useful when used in conjunction with Scheme IV because in step 3, the second amination

Step 2 - First amination using primary amine

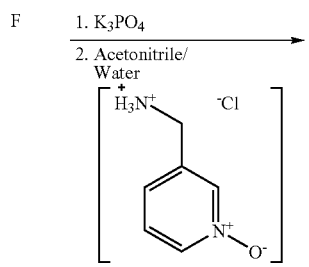

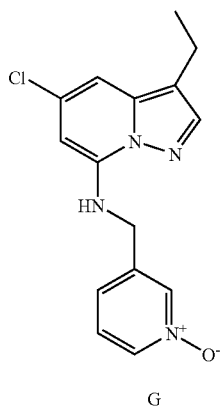

G

Step 3 - Second amidation with secondary amine

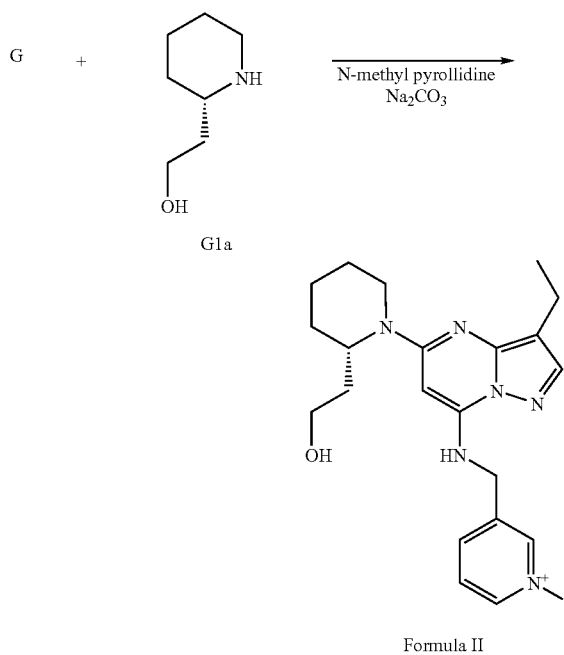

Formula II

EXAMPLES

The following solvents and reagents may be referred to by their abbreviations in parenthesis:

tetrahydrofuran: THF methanol: MeOH

HPLC: high pressure liquid chromatography mole: mol.

ee: enantiomeric excess—(weight of desired enantiomer recovered)/(weight of desired enantiomer present+weight of undesired enantiomer present)

All reagents were obtained from Aldrich or Acros and used as received unless otherwise noted.

Example 1

Preparation of Preparation of (S)-2-Piperidin-2-yl-Ethanol

Into a flask was placed N-acetyl-L-Leucine (8.65 g) dissolved in 10 ml of methanol. The solution was heated, maintaining the temperature at from 35° C. to 40° C. with stirring. A tetrahydrofuran (THF) solution prepared from 50 ml of THF and 12.9 g (0.1 mol.) of 2-piperidine-2-yl-ethanol (mixture of R and S isomers) was added to the methanol solution maintaining the temperature of the combined solutions at 35° C. to 40° C. An additional 30 ml of THF was added and the resulting mixture was heated and maintained at a temperature of from 50° C. to 55° C. for 30 minutes. The reaction mixture was cooled over two hours to 15° C. and held at that temperature for one hour, during which time salt precipitated. The precipitate was recovered by vacuum filtration and dried under vacuum at ambient temperature (about 25° C.). The recovered precipitate was tested for ee purity by HPLC through derivatization of the product with benzoyl chloride and found to be 94.5% ee S-isomer. A yield of 37.7% based on the weight of the unresolved alcohol starting material was calculated (11.4 g isolated S-isomer), accordingly a loss of about 25% S-isomer.

Purification of Precipitate

An aliquot of the precipitate salt thus formed (7.0 g) was suspended with stirring in a solvent comprising 50 ml of acetonitrile and 2.5 ml of methanol by heating the mixture to 55° C. and held for 30 minutes. The resultant suspension was cooled over a period of 2 hours to a temperature of 15° C. The resulting crystals were obtained by filtration and tested by HPLC for purity and a yield was calculated based on recovered weight. The precipitation yielded 6.7 g of precipitate (calculated yielded 95.7% based on starting precipitated complex) and had a isomeric purity of 97.7% ee based on HPLC analysis.

Conversion to Free Base

A salt of the piperidine ethanol is converted to the free base by dissolving 13 mmol. of the purified salt in 24 ml of 3N NaOH and stirring the resulting solution vigorously for about 1.5 hours. At the end of 1.5 hours of stirring, 7.5 ml of water is added to the solution. This mixture is then extracted with methylene chloride three times. The methylene chloride extracts are concentrated to yield approximately 13 mmol. of free piperidine ethanol. The chiral purity of the product is found to be the same as that of the original salt.

Comparative Example

The stereoisomer of the 2-Piperidin-2-yl-ethanol (Compound G1a) was prepared as described in the '878 publication in accordance with preparative Example 500, therein.

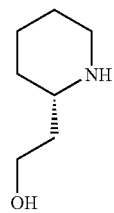

Compound G1a

Thus, a mixture of R and S enantiomers of piperidine-2-ethanol obtained from Acros and used as received (127 g, 980 mmol) was dissolved in 95% EtOH (260 mL). To the aliphatic alcohol solution was added to (S)-(+)-camphorsulfonic acid obtained from Acros (228.7 g, 1.0 eq.) in 95% EtOH (150 mL) and the resulting solution was warmed to reflux. To the warm solution was added $Et_2O$ (600 mL) and the solution cooled to room temperature and let stand 3 days. The resulting crystals were filtered and dried in vacuo (25 g): and analyzed by mp 173° C. (lit. 168° C.). The salt was then dissolved in NaOH (3M, 100 mL) and stirred 2 hours and the resulting solution was extracted with $CH_2Cl_2$ (5×100 mL). The combined organics were dried over $Na_2SO_4$, filtered and concentrated under reduced pressure to give (S)-piperidine-2-ethanol (7.8 g) a portion of which was recrystallized from $Et_2O$: mp=69-70° C. (lit. 68-69° C.); $[\alpha]_D=14.09°$ ($CHCl_3$, c=0.2). Overall yield of S-isomer isolated, based on initial weight of starting alcohol was 6.1%.

The above description of the invention is intended to be illustrative and not limiting. Various changes or modifications in the embodiments described herein may occur to those skilled in the art. These changes can be made without departing from the scope or spirit of the invention

What is claimed is:

1. A process for resolving the S-isomer of 2-piperidin-2-yl ethanol from a mixture of isomers, the process comprising:
   (a) combining a solution comprising a polar, aprotic organic solvent and a mixture of isomers of 2-piperidin-2-yl-ethanol with an aliphatic alcohol solution containing an amino acid resolving agent selected from N-acetyl-L-leucine and N-acetyl-L-methionine;
   (b) mixing the combined solutions with additional amounts of the polar, aprotic organic solvent used in Step "a" and warming the mixture to a temperature below the boiling point of either solvent in the mixture sufficient to promote dissolution of any solids present in the mixture;
   (c) cooling the mixture to a temperature which permits salt precipitation therefrom;
   (d) isolating the precipitated salt formed in step "c"; and
   (e) purifying the isolated salt from Step "d" by recrystallization or slurrying with a purifying solvent, and optionally repeating the recrystallization or slurrying step until the desired enantiomeric purity is achieved.

2. The process of claim 1 wherein the polar aprotic organic solvent used in said "combining" Step "a" is a solvent selected from tetrahydrofuran (THF), acetonitrile (ACN), acetone, and ethylacetate, and mixtures of two or more thereof.

3. The process of claim 1 wherein, wherein the aliphatic alcohol used in Step "a" is an alcohol having 5 carbon atoms or less.

4. The process of claim 2 wherein said polar aprotic organic solvent (PAO solvent) in step "a" is THF and the alcohol in step "a" is methanol.

5. The process of claim 1 wherein, said recrystallization step "e", when carried out, is carried out in a mixed solvent.

6. The process of claim 2 wherein, said recrystallization step "e", when carried out, is carried out in a mixed solvent.

7. The process of claim 3 wherein, said recrystallization step "e", when carried out, is carried out in a mixed solvent.

8. The process of claim 5 wherein, when carried out, said mixed solvent used in Step "e" is a mixture of a solvent selected from acetonitrile and THF and an aliphatic alcohol having 5 or fewer carbon atoms.

9. The process of claim 6 wherein, when carried out, said mixed solvent used in Step "e" is a mixture of a solvent selected from acetonitrile and THF and an aliphatic alcohol having 5 or fewer carbon atoms.

10. The process of claim 7 wherein, when carried out, said mixed solvent used in Step "e" is a mixture of a solvent selected from acetonitrile and THF and an aliphatic alcohol having 5 or fewer carbon atoms.

11. The process of claim 2 wherein, said Step "e" is carried out in a mixture comprising 19 volumes of acetonitrile and 1 volume of methanol.

12. The process of claim 3 wherein, said Step "e" is carried out in a mixture comprising 19 volumes of acetonitrile and 1 volume of methanol.

13. The process of claim 1 further comprising the steps of:
   (i) providing a mixture comprising redissolving or suspending a precipitated salt obtained from optional step "d" or step "e" in a solvent; and
   (ii) treating the mixture from step "i" with a base to yield (S)2-piperidine-2-yl-ethanol free base.

14. The process of claim 1 further including obtaining a precipitated salt from optional step "d" or optional step "e", and is introducing it into a reaction mixture containing a base, thereby providing (S)2-piperidine-2-yl-ethanol free base in situ in the reaction mixture.

15. The process of claim 1 wherein, the resolving agent in step "a" is N-acetyl-L-leucine.

16. The process of claim 9 wherein, the resolving agent in step "a" is N-acetyl-L-leucine.

17. The process of claim 16 wherein, the resolving agent is present in the step "a" solution in an amount sufficient to provide a solution of about 5 M in resolving agent.

18. The process of claim 1 wherein, the mixture of solvents used in Step "a", the combining step, comprises a volumetric ratio of polar aprotic organic solvent (PAO solvent):aliphatic alcohol of from about 2:1 PAO solvent:aliphatic alcohol to about 10:1 PAO solvent:aliphatic alcohol.

19. The process of claim 18 wherein the mixture of solvents used in Step "a" comprises a volumetric ratio of about 5:1 PAO solvent:aliphatic alcohol.

20. The process of claim 3 wherein the THF solution used in Step "a" comprises at least an amount of 2-piperidin-2-yl-ethanol sufficient to provide a 2M solution.

21. The process of claim 1 wherein the combined methanol and THF solutions in step "a" are maintained at a temperature of from about 20° C. to about 60° C.

22. The process of claim 21 wherein the combined methanol and THF solutions in step "a" are maintained at a temperature of from about 35° C. to about 40° C.

23. The process of claim 1 wherein the solution of step "b" is heated to a temperature of from about 30° C. to a temperature below the refluxing temperature of the solvent mixture.

24. The process of claim 23 wherein the solution of step "b" is heated to a temperature of from about 50° C. to about 55° C.

25. The process of claim 1 wherein said purification step "e" is carried out by heating the precipitate formed in step "d" in a mixture of 1 vol. eq. of methanol and 20 vol. eq. of acetonitrile to a temperature of about 55° C. and cooling it to a temperature of about 15° C.

26. The process of claim 1 wherein said purification step "e" is carried out by heating a slurry comprising a mixture of 1 vol. eq. of methanol, 20 vol. eq. of acetonitrile, and the precipitate formed in step "d" to a temperature of about 55° C., holding the slurry at temperature for a time sufficient to dissolve the impurities, and cooling the slurry to a temperature of about 15° C.

27. A process for making pyrazolo[1,5-a]pyrimidin-7-yl-amino compounds of Formula III

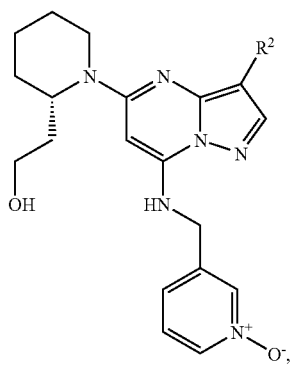

Formula III wherein $R^2$ is a linear, branched or cyclic alkyl group, the process comprising:
(a) combining a solution comprising a polar, aprotic organic solvent and a mixture of isomers of 2-piperidin-2-yl-ethanol with an aliphatic alcohol solution containing an amino acid resolving agent selected from N-acetyl-L-leucine and N-acetyl-L-methionine;
(b) mixing the combined solutions with additional amounts of the polar, aprotic organic solvent and warming the mixture to a temperature below the boiling point of either solvent in the mixture sufficient to promote dissolution of any solids present in the mixture;
(c) cooling the mixture to a temperature which permits the salt of compound G1a to precipitate therefrom,

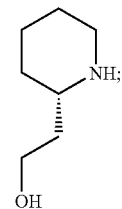

G1a (d) isolating the precipitated salt formed in step "c",
(e) purifying the salt from step "c" by slurrying the salt in a 10:1 by volume mixture of acetonitrile (ACN) and methanol;
(f) liberating the free base alcohol G1a from the salt prepared in purifying Step "e"; and
(g) reacting the free base alcohol from Step "e" with the compound of Formula G1,

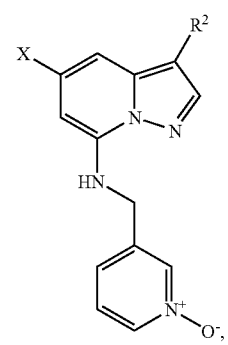

G1 wherein "X" is a halogen or sulfonyl leaving group.

28. The process of claim 27 wherein, "$R^2$" is an ethyl-substituent and X is $Cl^-$.

29. The process of claim 27 wherein, the polar, aprotic organic solvent in Step "a" is selected from tetrahydrofuran (THF), acetonitrile (ACN), ethyl acetate and acetone.

30. The process of claim 29 wherein, the aliphatic alcohol in Step "a" is selected from aliphatic alcohols having 5 carbon atoms or less.

31. The process of claim 29 wherein, the aliphatic alcohol in Step "a" is methanol.

32. The process of claim 27 wherein, said liberating step "e" is carried out by combining the isolated resolved salt with a reaction mixture in the presence of a base and liberating the free base alcohol in situ.

33. The process of claim 27 wherein, said liberating step "e" is carried out by treating the isolated resolved salt with a base, crystallizing the free base alcohol out of solution, and isolating the free base crystals by filtration.

34. A process for resolving the S-isomer of 2-piperidin-2-yl ethanol from a mixture of isomers, the process comprising:
(a) combining a tetrahydrofuran (THF) solution containing a mixture of isomers of 2-piperidin-2-yl ethanol with a methanol solution containing N-acetyl-L-leucine;
(b) mixing the combined solutions with additional THF and warming the mixture to a temperature below the boiling point of either solvent in the mixture;

(c) cooling the mixture to a temperature which permits salt precipitation therefrom;
(d) isolating the precipitated salt formed in step "c"; and
(e) optionally recrystallizing the salt.

35. The process of claim 34 further comprising the steps of:
(i) dissolving or suspending a precipitated salt obtained from optional step "d" or optional step "e" in a solvent; and
(ii) treating the mixture from step "i" with a base to yield (S)2-piperidine-2-yl-ethanol free base.

36. The process of claim 35 wherein said solvent used in Step "i" is a sodium hydroxide aqueous solution, thereby providing the solvent and base treatment in a single step.

37. The process of claim 27 wherein, the mixture of solvents used in Step "a", the combining step, comprises a volumetric ratio of polar aprotic organic solvent (PAO solvent):aliphatic alcohol of from about 2:1 PAO solvent:aliphatic alcohol to about 10:1 PAO solvent:aliphatic alcohol.

38. The process of claim 37 wherein, the resolving agent is present in the step "a" solution in an amount sufficient to provide a solution of about 5 M in resolving agent.

39. The process of claim 27 wherein said purification step "e" is carried out by heating the precipitate formed in step "d" to a temperature of about 55° C. and cooling it to a temperature of about 15° C.

* * * * *